(12) United States Patent
Lee et al.

(10) Patent No.: US 9,099,543 B2
(45) Date of Patent: Aug. 4, 2015

(54) NANOWIRE SENSOR HAVING NANOWIRE OF NETWORK STRUCTURE

(75) Inventors: Jeong Soo Lee, Pohang-si (KR); Yoon Ha Jeong, Pohang-si (KR); Tai Uk Rim, Pohang-si (KR); Chang Ki Baek, Pohang-si (KR); Sung Ho Kim, Pohang-si (KR); Ki Hyun Kim, Ulsan (KR)

(73) Assignee: POSTECH ACADEMY-INDUSTRY FOUNDATION, Pohang-Si, Gyeongsangbuk-Do (KR)

( * ) Notice: Subject to any disclaimer, the term of this patent is extended or adjusted under 35 U.S.C. 154(b) by 0 days.

(21) Appl. No.: 14/111,727

(22) PCT Filed: Mar. 19, 2012

(86) PCT No.: PCT/KR2012/001964
§ 371 (c)(1),
(2), (4) Date: Oct. 14, 2013

(87) PCT Pub. No.: WO2012/141431
PCT Pub. Date: Oct. 18, 2012

(65) Prior Publication Data
US 2014/0034907 A1    Feb. 6, 2014

(30) Foreign Application Priority Data
Apr. 14, 2011   (KR) .................. 10-2011-0034860

(51) Int. Cl.
| | | |
|---|---|---|
| H01L 27/14 | (2006.01) |
| H01L 21/00 | (2006.01) |
| H01L 29/775 | (2006.01) |
| G01N 27/06 | (2006.01) |
| G01N 27/327 | (2006.01) |
| G01N 33/487 | (2006.01) |
| H01L 29/66 | (2006.01) |
| B82Y 40/00 | (2011.01) |

(52) U.S. Cl.
CPC .............. *H01L 29/775* (2013.01); *G01N 27/06* (2013.01); *G01N 27/3278* (2013.01); *G01N 33/48707* (2013.01); *H01L 29/66477* (2013.01); *B82Y 40/00* (2013.01)

(58) Field of Classification Search
None
See application file for complete search history.

(56) References Cited

U.S. PATENT DOCUMENTS

| | | | |
|---|---|---|---|
| 2006/0185980 A1 | 8/2006 | Fukuda | |
| 2009/0152598 A1 | 6/2009 | Baek et al. | |
| 2013/0337567 A1* | 12/2013 | Shin et al. ....................... 436/63 |

FOREIGN PATENT DOCUMENTS

| | | |
|---|---|---|
| CN | 101046458 | 10/2007 |
| CN | 101685077 | 3/2010 |

(Continued)

OTHER PUBLICATIONS

International Search Report for International Application No. PCT/KR2012/001964, dated Nov. 30, 2012.

*Primary Examiner* — Bilkis Jahan
*Assistant Examiner* — Kevin Quinto
(74) *Attorney, Agent, or Firm* — Kile Park Reed & Houtteman PLLC (57) ABSTRACT

A nanowire sensor having a nanowire in a network structure includes: source and drain electrodes formed over a substrate; a nanowire formed between the source and drain electrodes and having a network structure in which patterns of intersections are repeated; and a detection material fixed to the nanowire and selectively reacting with a target material introduced from outside.

18 Claims, 14 Drawing Sheets

(56) References Cited

FOREIGN PATENT DOCUMENTS

| CN | 102180518 | 9/2011 |
|---|---|---|
| CN | 102235988 | 11/2011 |
| JP | 2006-505806 | 2/2006 |
| KR | 10-2009-0065124 | 6/2009 |
| KR | 10-2011-0010929 | 2/2011 |
| KR | 10-1040083 | 6/2011 |
| WO | 2004/044586 | 5/2004 |

* cited by examiner

NANOWIRE SENSOR HAVING NANOWIRE OF NETWORK STRUCTURE

BACKGROUND OF THE INVENTION

1. Field of the Invention

The present invention relates to a nanowire sensor using a nanowire, and more particularly, to a nanowire sensor having a nanowire in a network structure, which uses a nanowire in a network structure including repeated patterns instead of a straight nanowire, thereby obtaining high efficiency and structural stability.

2. Description of the Related Art

An electrochemical sensor is an element which converts a physical or chemical characteristic of a target material into an electrical signal. The electrochemical sensor is expected to be widely used as a biosensor, chemical sensor or environmental sensor, depending on a target material.

In order to sense and analyze a target material using an electrochemical sensor, the electrochemical sensor must have such a high sensitivity that a signal is significantly changed for a fine characteristic of the target material. Furthermore, the electrochemical sensor must have chemical stability for chemical composition of body fluid and physical stability for a flow of fluid. Furthermore, an existing measurement platform must be used to facilitate the use of the electrochemical sensor, and the electrochemical sensor must have a structure which may be easily mass-produced for economic feasibility and practicality.

In this aspect, a silicon sensor fabricated through an existing semiconductor process is the most suitable for requirements of the electrochemical sensor. Among the requirements, a nanowire channel has a one-dimensional structure and an excellent gate control ability, and has a higher ratio of area to volume than a flat panel silicon channel, thereby obtaining a high sensitivity. Thus, much research has been conducted on the nanowire channel.

Figure 1:
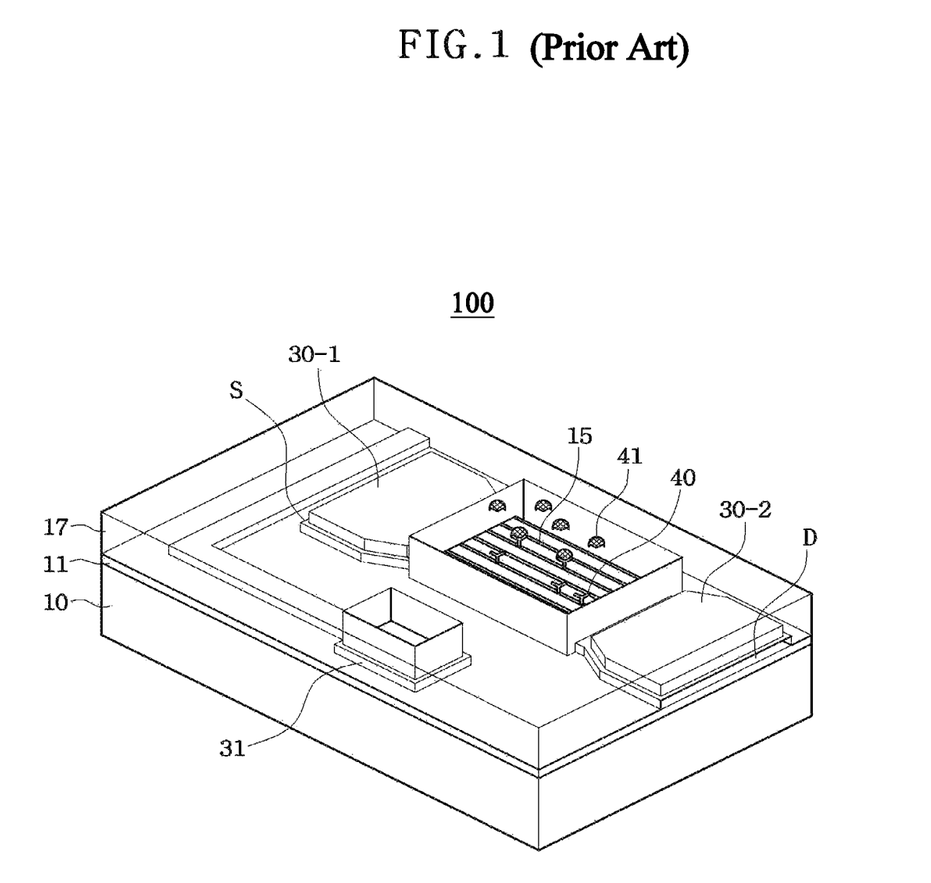
FIG. 1 is a diagram illustrating a conventional nanowire sensor using a nanowire.

FIG. 1 is a diagram illustrating a conventional nanowire sensor using a nanowire.

Referring to FIG. 1, the conventional nanowire sensor includes a detection material 40 attached on a gate insulating layer 15 over nanowires formed between a source electrode region S and a drain electrode region D, and performs sensing by changing conductance of a nanowire channel region through charge of a target material 41 which is selectively attached to the detection material. At this time, a separate underwater gate electrode 31 may be provided to fix the potential of a solution.

In the case of the conventional nanowire sensor, the silicon nanowire to which the detection material is fixed may be formed in a bottom-up type or top-down type. The bottom-up type silicon nanowire and the top-down type silicon nanowire have the following problems.

In the case of the bottom-up type nanowire, silicon nanowires formed through a semiconductor process technology such as CVD (Chemical Vapor Deposition) are aligned at specific positions so as to fabricate a sensor. At this time, since the nanowires are not easily synthesized and aligned, there are difficulties in mass-producing the nanowire sensor.

In the case of the top-down type nanowire fabricated through a silicon-on insulator (SOI) substrate, an excellent electric characteristic may be obtained, but there are difficulties in implementing a nanowire having a smaller thickness than the bottom-up type nanowire due to the limit of exposure technology. Furthermore, when a gate-all-around device is implemented to acquire a high sensitivity, nanowires may be bent or collapse in case where the nanowires have a length of several hundred nm or more. Furthermore, the top-down type nanowire is structurally unstable for a flow of fluid.

A general nanowire sensor has a structure in which straight nanowire bundles are connected to a source and drain thereof. At this time, since one target material among arbitrarily-arranged target materials has an influence on only one nanowire, the number of nanowire bundles must be increased to obtain a high sensitivity. Thus, the number of elements with respect to area may be decreased to thereby make it difficult to reduce a cost.

SUMMARY OF THE INVENTION

Accordingly, the present invention has been made in an effort to solve the problems occurring in the related art, and an object of the present invention is to provide a nanowire sensor which includes a nanowire formed in a network structure so as to have a larger exposed surface area than a nanowire sensor including a straight nanowire, thereby increasing the probability that a detection material will be attached to the nanowire and improving measurement sensitivity.

In order to achieve the above object, according to one aspect of the present invention, a nanowire sensor having a nanowire in a network structure includes: source and drain electrodes formed over a substrate; a nanowire formed between the source and drain electrodes and having a network structure in which patterns of intersections are repeated forming a generally uniform grid; and a detection material fixed to the nanowire and selectively reacting with a target material introduced from outside.

According to another aspect of the present invention, a method for fabricating a nanowire sensor having a nanowire in a network structure includes: sequentially forming an insulating layer and a silicon layer over a substrate; forming a source electrode region, a drain electrode region and a nanowire pattern over the silicon layer using a lithography process; implanting ions into the source electrode region and the drain electrode region; removing a lower support layer of the nanowire pattern through a wet etching process; forming a gate insulating layer outside the source electrode region, the drain electrode region and the nanowire; forming a metal electrode over the source electrode region and the drain electrode region; forming an upper insulating layer over the metal electrode of the nanowire, and removing the upper insulating layer to expose the gate insulating layer of the nanowire; and fixing a detection material, which is to react with a target material injected from outside, to the exposed nanowire pattern, wherein the nanowire pattern is formed in a network structure in which patterns of intersections are repeated between the source electrode region and the drain electrode region.

BRIEF DESCRIPTION OF THE DRAWINGS

The above objects, and other features and advantages of the present invention will become more apparent after a reading of the following detailed description taken in conjunction with the drawings, in which.

DETAILED DESCRIPTION OF PREFERRED EMBODIMENTS

Reference will now be made in greater detail to a preferred embodiment of the invention, an example of which is illustrated in the accompanying drawings. Wherever possible, the same reference numerals will be used throughout the drawings and the description to refer to the same or like parts.

Figure 2:
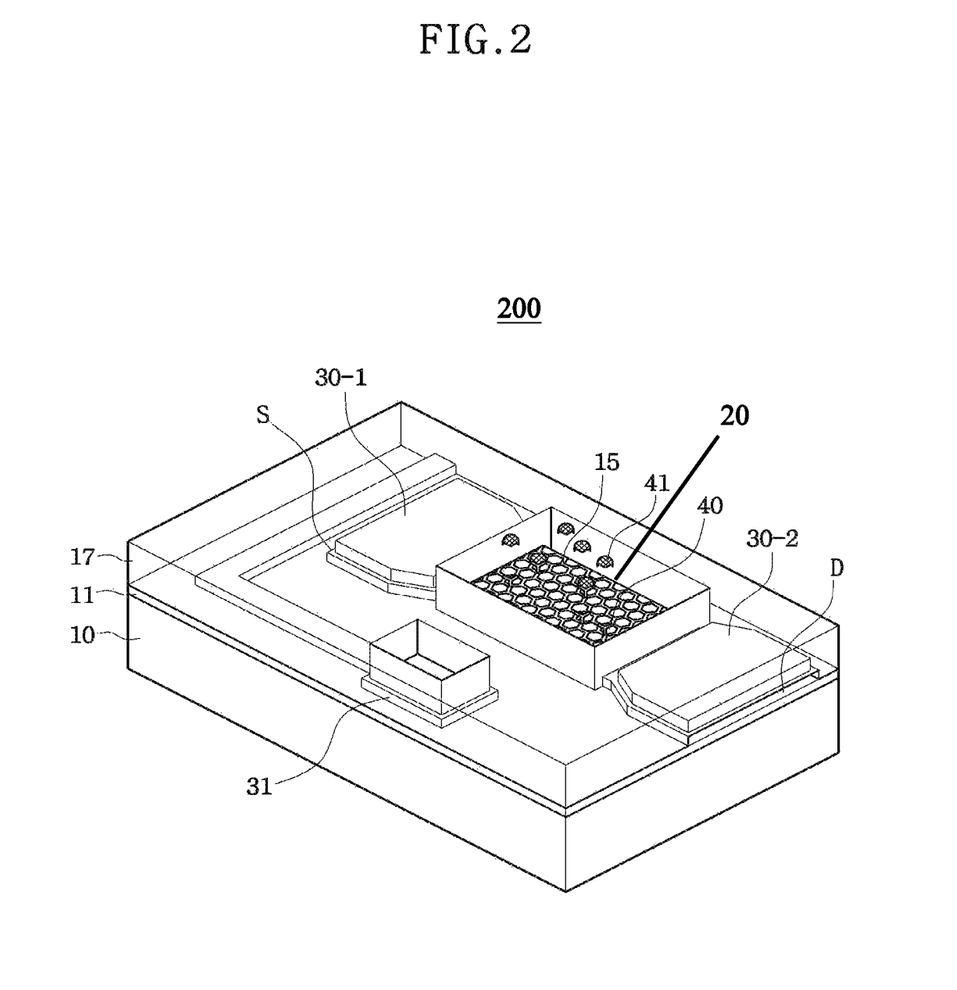
FIG. 2 is a diagram for explaining the structure and operation principle of a nanowire sensor having a nanowire grid forming a network structure according to an embodiment of the present invention.

FIG. 2 is a diagram for explaining the structure and operation principle of a nanowire sensor having a nanowire in a network structure according to an embodiment of the present invention.

Referring to FIG. 2, the nanowire sensor 200 having a nanowire in a network grid structure according to the embodiment of the present invention includes a source electrode 30-1 and drain electrode 30-2 formed over a substrate, a nanowire grid 20 formed between the source electrode 30-1 and the drain electrode 30-2 and having a network structure in which patterns of intersections are repeated, and a detection material 40 fixed to the nanowire and selectively responding to a target material introduced from outside.

The substrate may include a semiconductor, polymer or nonconductor substrate, and the nanowire may include a silicon, compound semiconductor or polymer nanowire.

The nanowire sensor 200 of FIG. 2 includes the same components as those of the conventional nanowire sensor 100 of FIG. 1, except that the nanowire of the nanowire sensor 200 has a network structure.

That is, the nanowire sensor 200 having a nanowire in a network structure according to the embodiment of the present invention includes multiple bundles of short nanowires connected in a network structure, unlike the conventional nanowire sensor.

The nanowire is formed in a network structure in which patterns of intersections are successively repeated in an X-shape, Y-shape, T-shape or cross shape.

At this time, the nanowire may have a width of 5 nm to 1μ, and an interval between the intersections at which the patterns are repeated may be set in the range of 10 nm to 1μ.

When the nanowire is formed in a network structure instead of a straight-line structure, measurement sensitivity may be improved because the detection material 40 formed on the nanowire has a large area to which the target material 41 is attached. Furthermore, when the nanowire is formed in such a manner that multiple bundles of short nanowires are connected in a network structure, a gate-all-around device may be implemented with structural stability. Such characteristics will be described with reference to FIGS. 3 and 4.

Figure 3A:
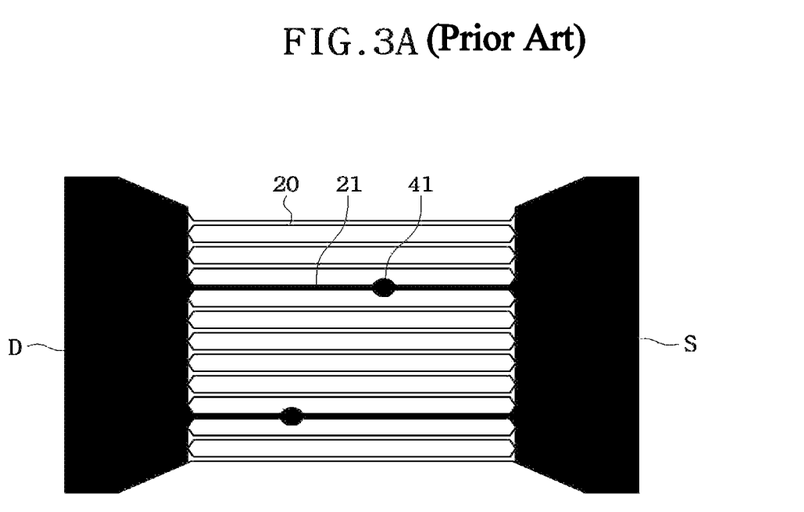
FIGS. 3A and 3B are diagrams for comparatively explaining operation characteristics of the conventional nanowire sensor and the nanowire sensor having a nanowire in a network structure according to the embodiment of the present invention.
Figure 3B:
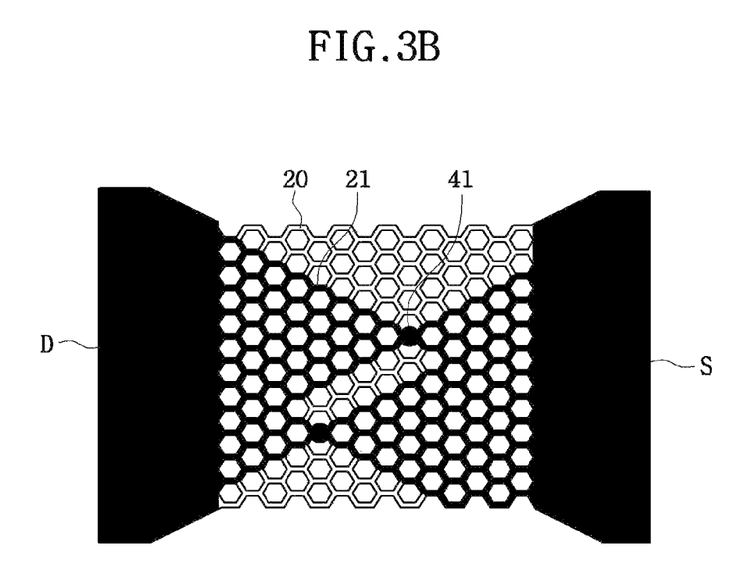
Figure 4:
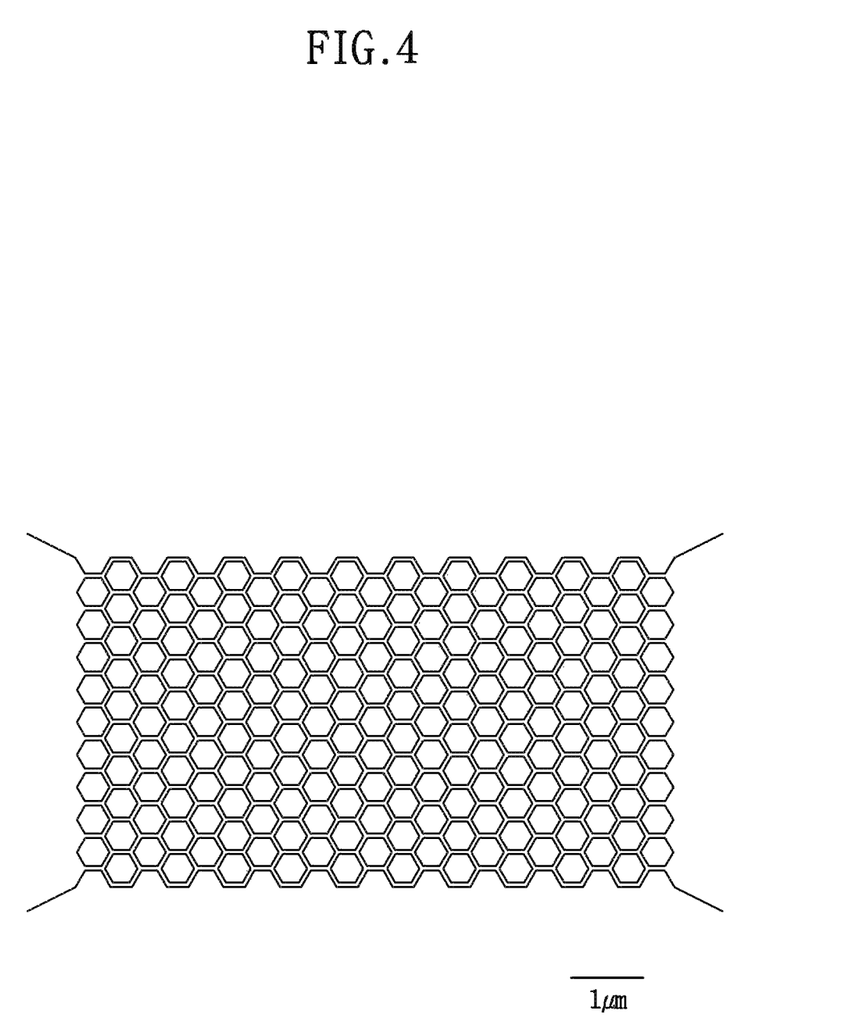
FIG. 4 is an electron microscope photograph for explaining structural stability when a lower support layer of the nanowire in a network structure is not provided.

FIGS. 3A and 3B are diagrams for comparatively explaining the operation characteristics of the conventional nanowire sensor and the nanowire sensor having a nanowire in a network structure according to the embodiment of the present invention. FIG. 4 is an electron microscope photograph for explaining structural stability when a lower support layer of the nanowire in a network structure is not provided.

Referring to FIG. 3A, the conventional nanowire sensor having a straight nanowire includes a target material 41 attached to the top or side surface of a nanowire 20, and operates according to a method in which electrons or holes gather around the nanowire channel, to which the target material is attached, through electrical charge of the target material, thereby improving conductance. At this time, the nanowire to which the target material is attached among the entire nanowires becomes a region 21 which is influenced by the target material.

In the conventional nanowire sensor using a straight nanowire, when a target material is attached to one nanowire among the multiple bundles of nanowires, only the nanowire to which the target material is attached has an effect on the total conductance. Thus, the measurement sensitivity inevitably decreases.

On the other hand, referring to FIG. 3B, the nanowire sensor having a nanowire in a network structure according to an embodiment of the present invention may acquire a high sensitivity because all shortest-path nanowires between the source and drain regions, passing through a part to which the target material 41 is attached, have an effect on the total conductance.

The nanowire sensor having a nanowire in a network structure according to the embodiment of the present invention includes two or more paths having the same nanowire length among paths passing through one intersection of the nanowire between the source electrode region and the drain electrode region.

Thus, the conductance of the nanowire is changed for all shortest-path paths (indicated by thick lines) between the source electrode region and the drain electrode region, passing through the part to which the target material 41 is attached, which makes it possible to improve measurement sensitivity.

In the conventional nanowire sensor using a straight nanowire, when the nanowire has a small length, an area to which a target material is to be attached may be reduced, and the influence on an element by the target material may be stochastically reduced. When the nanowire has a large length, the nanowire may be bent in case where the bottom of the nanowire is not supported.

However, in the nanowire sensor having a nanowire in a network structure according to the embodiment of the present invention, since the short nanowires are tangled through the intersections, the structural strength of the nanowires is improved. For example, in the case of a network structure in short nanowires form Y-shaped intersections having an internal angle of 120 degrees, vertical and horizontal forces applied to an intersection are uniformly distributed in three directions. Thus, the nanowires may be more stably supported than the straight nanowires, without being bent.

Thus, in the nanowire sensor having a nanowire in a network structure according to the embodiment of the present invention, the bottom of the nanowires may not be attached to the top of the substrate, but may be spaced at a predetermined interval.

When the nanowires are formed in such a manner that the bottoms of the nanowires are not supported, the bottoms of the nanowires are exposed to a solution containing a target material, thereby increasing the total exposed surface area of the nanowires. The conductance of the nanowires may be changed by a target material attached to the bottoms of the nanowires.

The structural stability of the nanowires in a network structure may facilitate the fabrication of a nanowire sensor with a stacked structure, which is implemented using a wafer in which a plurality of silicon layers divided by a silicon-germanium or silicon insulating layer are stacked. Thus, it is possible to further improve the integration degree of the element.

Furthermore, the nanowires in a network structure may be implemented between a source and drain which are disposed at a smaller interval than in other nanowires having the same length. Thus, the density of regions covered by the nanowires among regions between the source and drain, which are exposed to the solution containing the target material, may be increased to thereby increase the integration degree of the element within a limited area.

Figure 5:
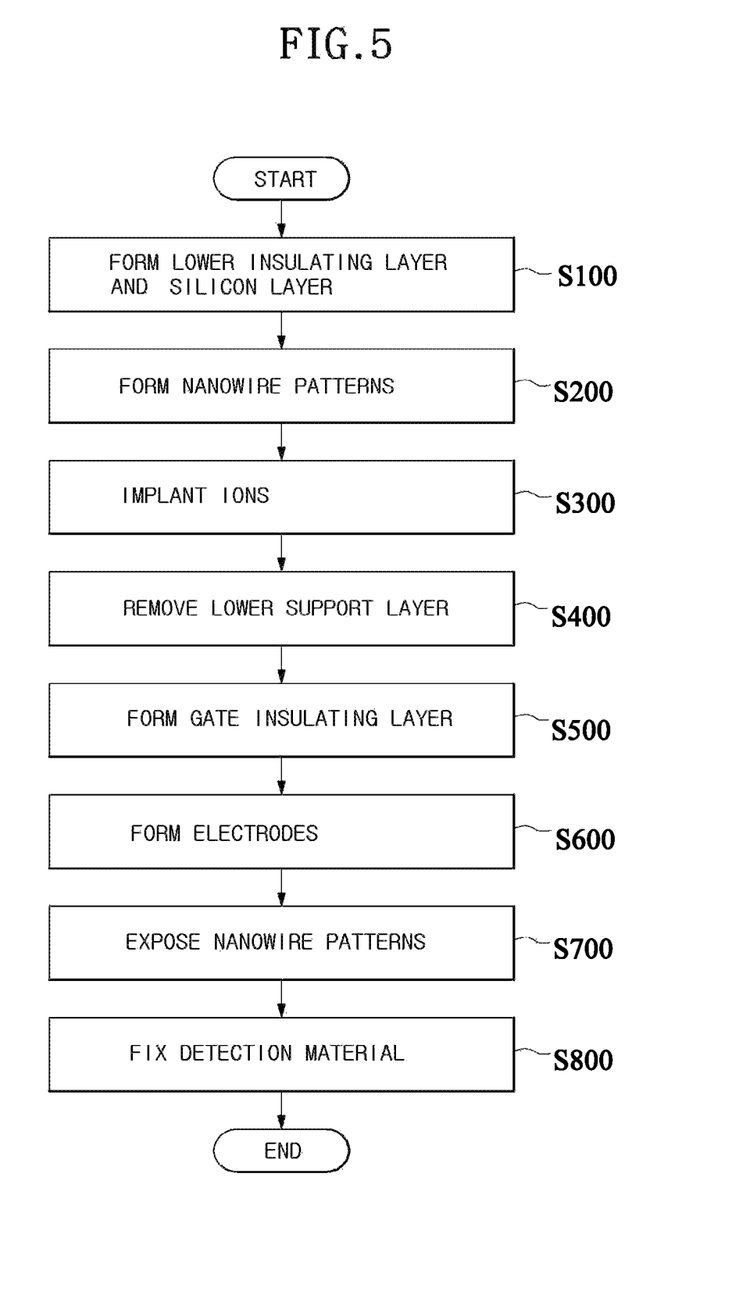
FIG. 5 is a flowchart for explaining a method for fabricating a nanowire sensor having a nanowire in a network structure according to an embodiment of the present invention.

FIG. 5 is a flowchart for explaining a method for fabricating a nanowire sensor having a nanowire in a network structure according to an embodiment of the present invention. FIGS. 6 to 13 are cross-sectional and plan views illustrating the respective processes of the method for fabricating a nanowire sensor having a nanowire in a network structure according to the embodiment of the present invention.

Referring to FIGS. 5 to 13, the method for fabricating a nanowire sensor having a nanowire in a network structure according to the embodiment of the present invention will be described.

As illustrated in FIGS. 5 to 13, the method for fabricating a nanowire sensor having a nanowire in a network structure according to the embodiment of the present invention includes forming a lower insulating layer and a silicon layer at step S100, forming nanowire patterns at step S200, implanting ions at step S300, removing a lower support layer at step S400, forming a gate insulating layer at step S500, forming electrodes at step S600, exposing the nanowire patterns at step S700, and fixing a detection material at step S800.

Figure 6:
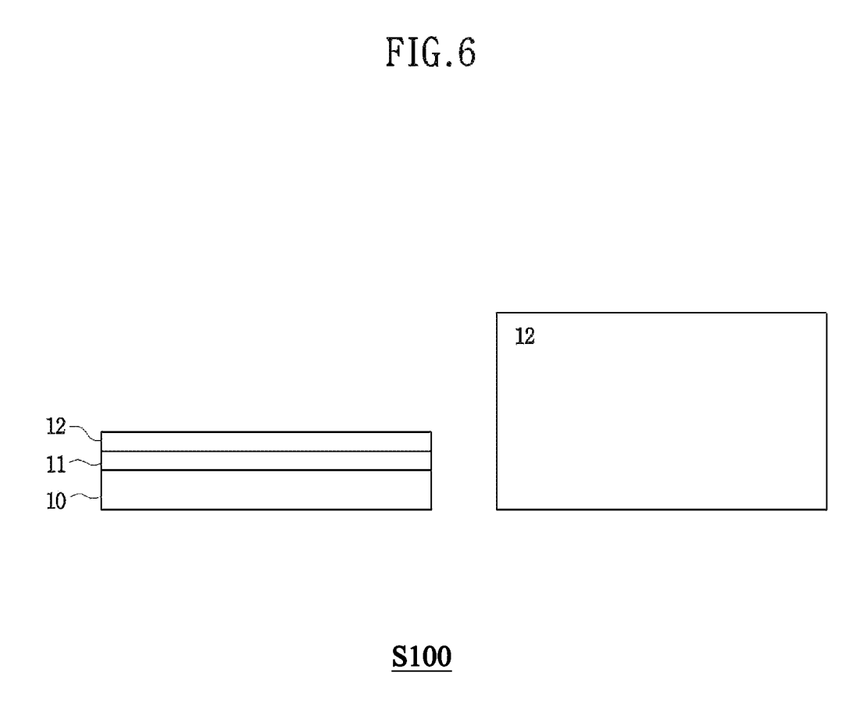
FIGS. 6 to 13 are cross-sectional and plan views illustrating the respective processes of the method for fabricating a nanowire sensor having a nanowire in a network structure according to the embodiment of the present invention.

At the step S100, a lower insulating layer 11 is formed over a substrate 10, and a silicon layer 12 doped at a low concentration is then formed over the lower insulating layer 11.

Figure 7:
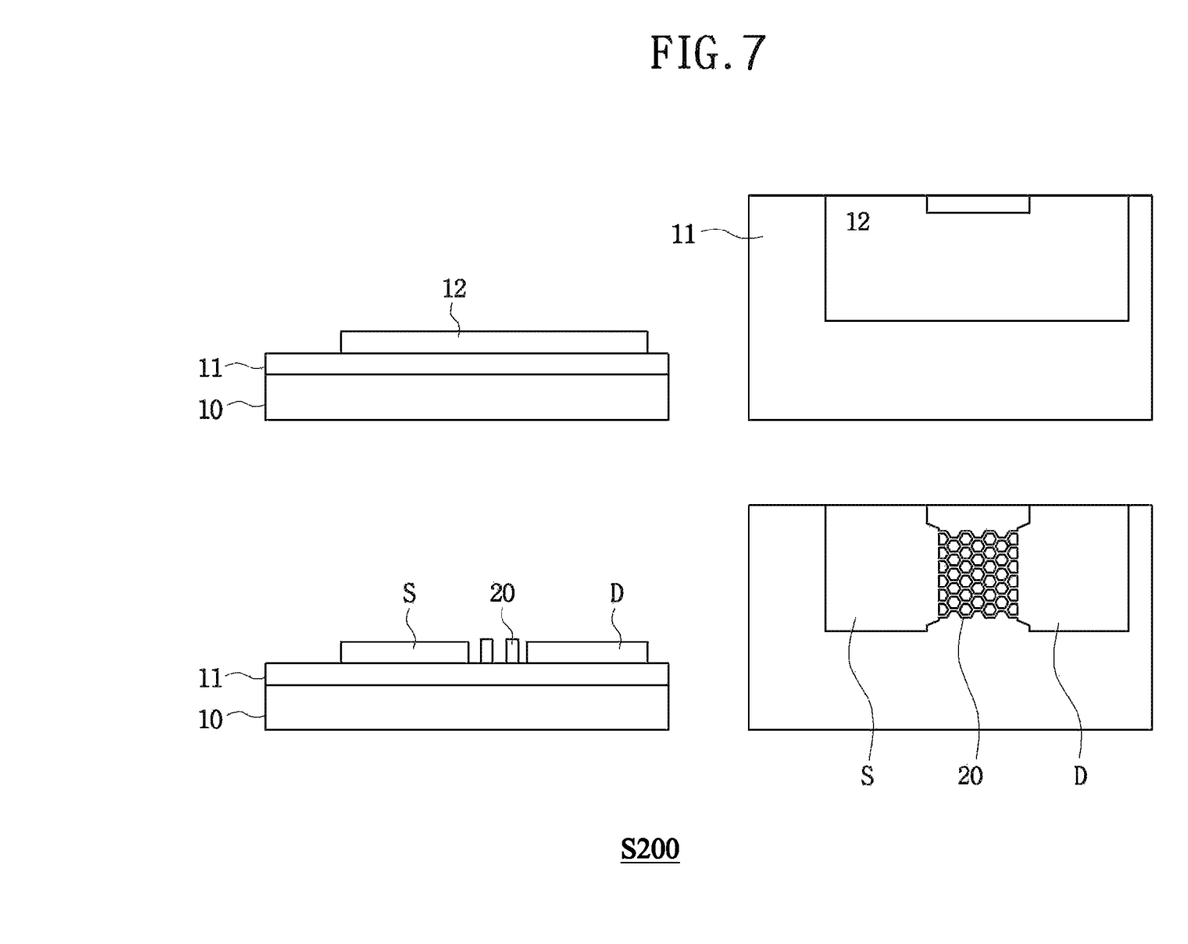

At the step S200, an active region including a source electrode region S, a drain electrode region D, and a nanowire region 20 is patterned over the silicon layer 12 through a lithography process, and nanowire patterns are formed through an etching process.

At this time, the nanowire region may be formed at one time or two times through a formation process for the source electrode region S and the drain electrode region D.

Figure 8:
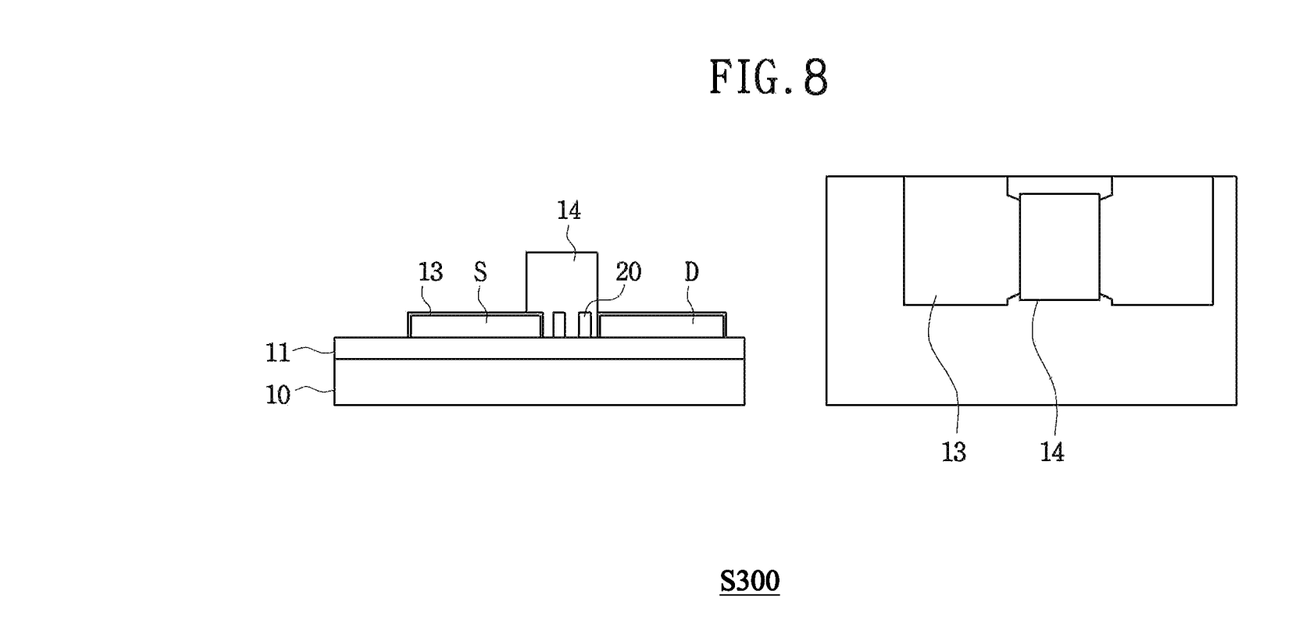

At the step S300, ions are implanted to increase the conductance of the source electrode region S and the drain electrode region D, which are formed in an elongated shape.

At this time, the ions may be implanted at a high concentration, and may not be implanted into a region where the patterns of the nanowires 20 are formed.

For this operation, a thermal oxidation process and a thin film formation process are used to form a thin ion leakage prevention layer 13 over the source electrode region S and the drain electrode region D such that the implanted ions do not escape, and a thick ion implant prevention layer 14 is formed over the nanowire region 20 such that ions are not implanted into the nanowire region.

Figure 9:
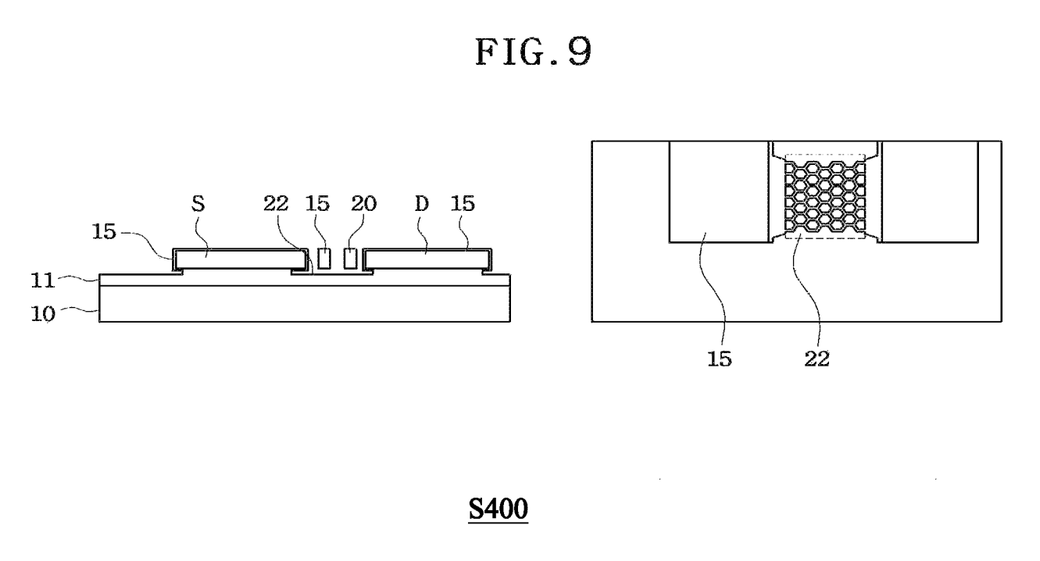

Then, the step S400 is performed to remove the lower support layer of the nanowire patterns through a wet etching process. That is, the lower support layer of the nanowires is removed through a wet etching process, in order to form a gate-all-around structure.

At this time, the thickness and width of the nanowires may be reduced through a process of forming an oxide layer on the silicon layer 12 using a furnace or rapid thermal processor (RTP) and then removing the oxide layer. Simultaneously, the silicon oxide layer of the nanowire support layer may be removed.

Figure 10:
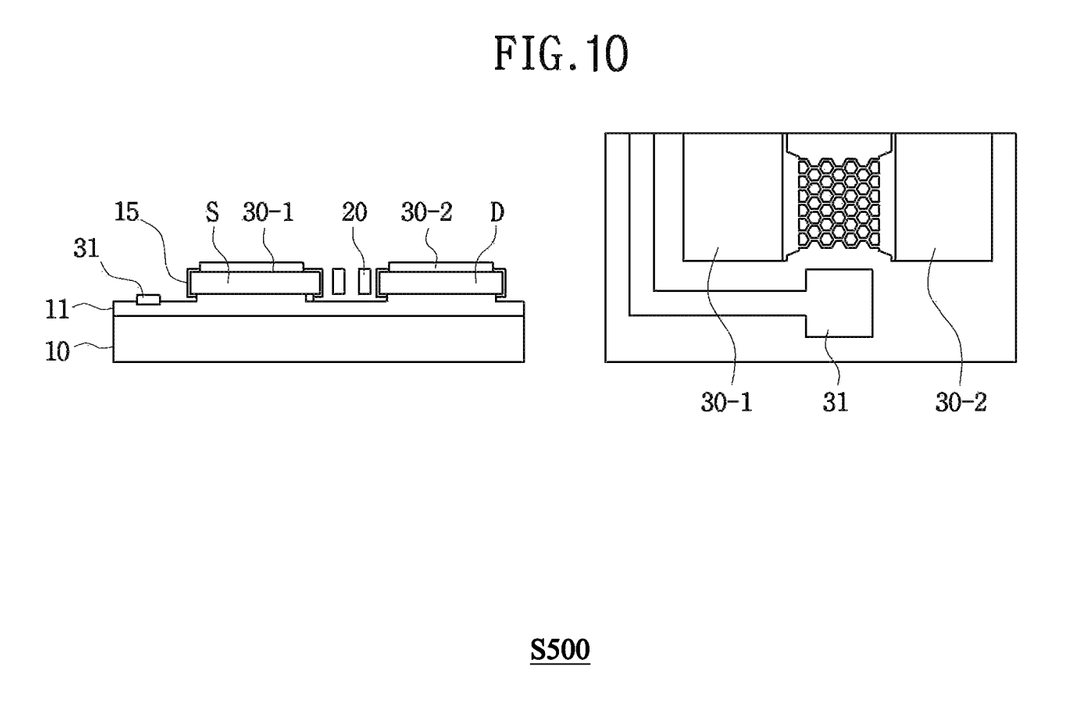

At the step S500, a gate insulating layer is formed outside the source electrode region, the drain electrode region and the nanowires so as to electrically insulate a channel region of the nanowires from a solution outside the nanowires. A chemical group required for attaching the detection material is exposed to the surface of the gate insulating layer, and a separate metal may be used.

Furthermore, the nanowire sensor may be applied as a sensor without the gate insulating layer, if necessary. The gate insulating layer may be formed only outside the nanowires.

Figure 11:
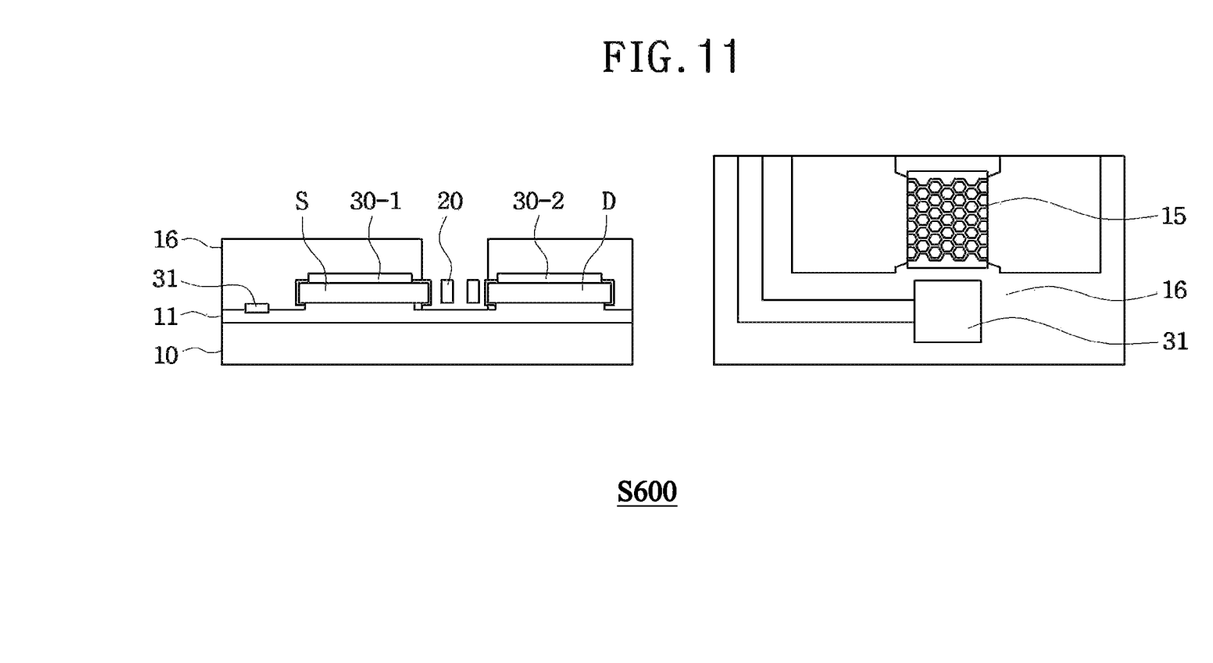

At the step S600, a source electrode 30-1 and a drain electrode 30-2 are formed over the source electrode region S and the drain electrode region D.

At this time, since the gate insulating layer 15 is already formed over the source electrode region S and the drain electrode region D, a process of removing the gate insulating layer 15 must be preceded. Furthermore, a separate underwater gate electrode 31 is additionally formed over the lower insulating layer 11 formed over the substrate 10, and then exposed to a solution containing a target material so as to directly apply a potential to the solution.

Figure 12:
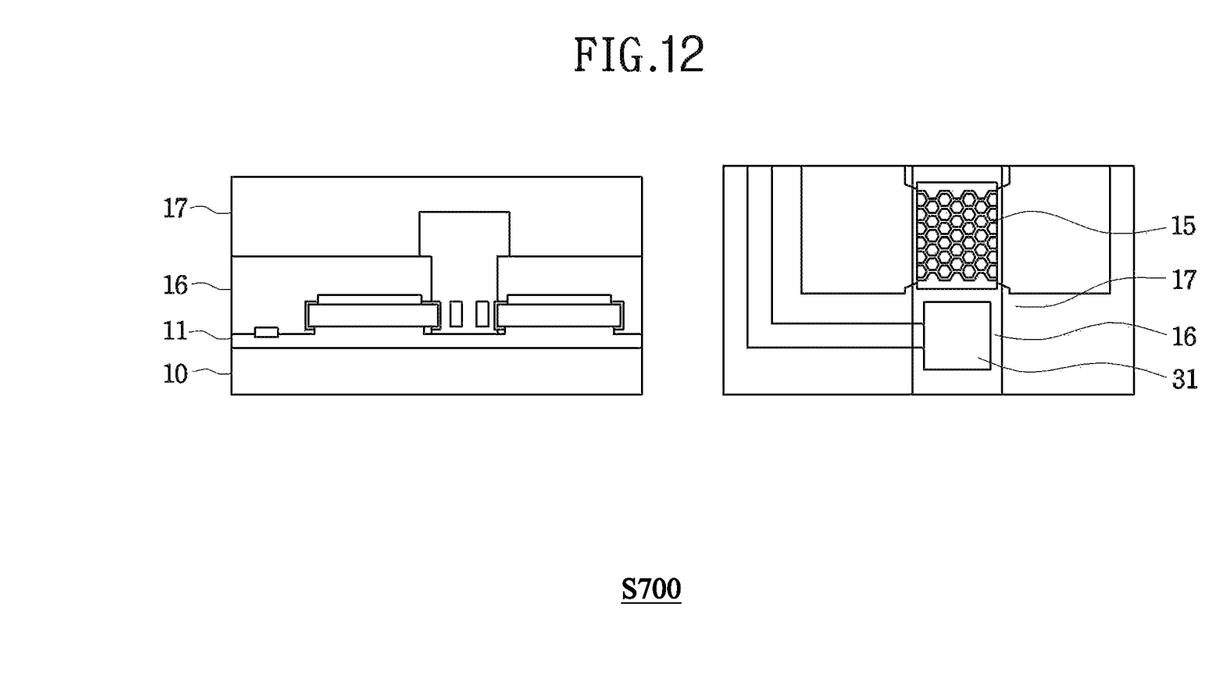

At the step S700, an upper insulating layer 16 for insulating the solution containing the target material from the metal electrodes is additionally formed over the source electrode region S, the drain electrode region D and a connection wire between the source electrode 30-1 and the drain electrode 30-2. Then, the upper insulating layer 16 is removed to expose the gate insulating layer of the nanowires.

Figure 13:
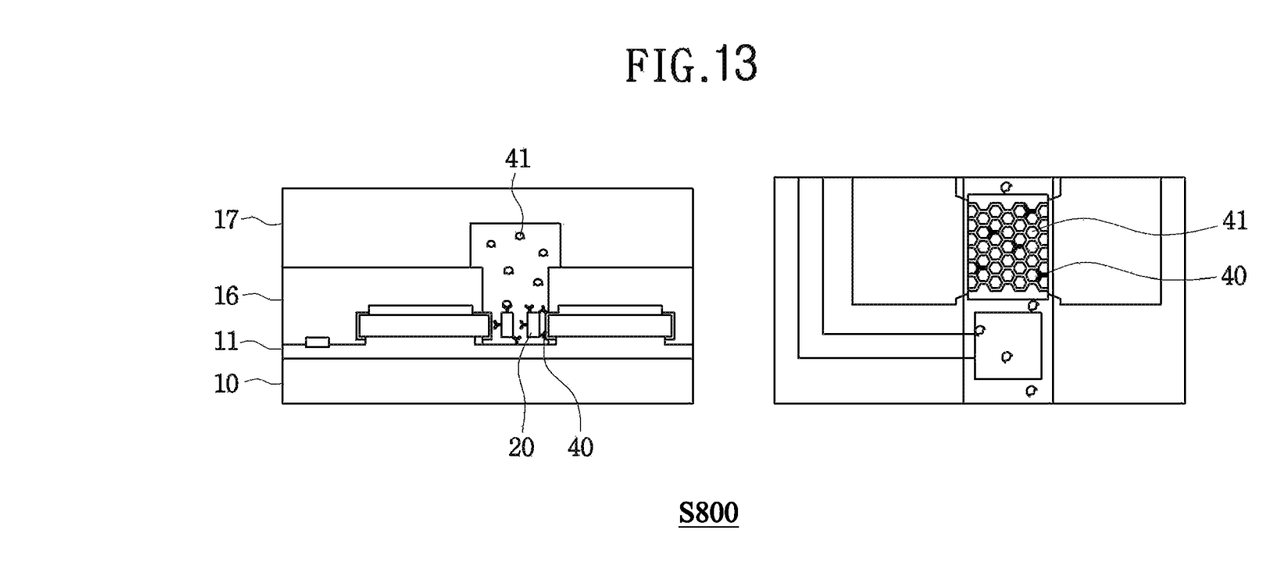

At the step S800, a surface chemical group of the nanowires is used to fix a detection material 40, which is to react with the target material 41 injected from outside, to a nanowire pattern.

At this time, a fluid channel layer 17 is formed over the insulating layer 16, and a channel through which the solution containing the target material 41 flows may be formed through a space among the fluid channel layer 17, the nanowire pattern and the underwater gate electrode 31, thereby protecting the solution from pollutants in the air.

Among the above-described steps, the sequence of the steps S200, S300, S400 and S500 may be changed in order to increase the sensitivity of the nanowire sensor and reduce a signal-to-noise ratio.

According to the embodiments of the present invention, the nanowire sensor having a nanowire in a network structure has a larger surface area than a nanowire sensor using a straight nanowire and thus increases the probability that a target material is to be attached to the nanowire. Furthermore, since the nanowire sensor may more sensitively sense changes in conductance or capacitance of the nanowire by the attached target material, the sensitivity of the sensor may be improved.

Furthermore, although the channel has a large length, the nanowire is not bent or deformed, but maintains an existing structure due to the stability of the network structure, such that the target material and the detection material may react with each other even at the side and bottom of the nanowire, Thus, the nanowire sensor may obtain a higher sensitivity.

Although a preferred embodiment of the present invention has been described for illustrative purposes, those skilled in the art will appreciate that various modifications, additions and substitutions are possible, without departing from the scope and the spirit of the invention as disclosed in the accompanying claims.

What is claimed is:

1. A nanowire sensor having a nanowire in a network grid structure, comprising:
   source and drain electrodes formed over a substrate;
   a nanowire grid formed between the source and drain electrodes and having a network structure in which patterns of intersections are repeated forming the network grid structure; and
   a detection material fixed to the nanowire grid and selectively reacting with a target material introduced from outside.

2. The nanowire sensor of claim 1, wherein the substrate comprises at least one of a semiconductor, a polymer and a nonconductor substrate.

3. The nanowire sensor of claim 1, wherein the nanowire grid comprises at least one of a silicon, a chemical semiconductor and a polymer nanowire.

4. The nanowire sensor of claim 1, wherein the nanowire grid is formed in at least one of an X-shape, a Y-shape, a T-shape and a cross-shape, and formed in a network grid structure in which patterns of intersections are successively repeated.

5. The nanowire sensor of claim 1, wherein the nanowire grid has a width of 5 nm to 1 µm.

6. The nanowire sensor of claim 1, wherein an interval between the intersections at which the patterns are repeated is set in the range of 10 nm to 1 µm.

7. The nanowire sensor of claim 1, wherein the bottom of the nanowire grid is not attached to the top of the substrate, but spaced at a predetermined interval from the top of the substrate.

8. The nanowire sensor of claim 1, wherein in two or more of paths passing through one intersection over the nanowire grid between the source electrode region and the drain electrode region, the nanowire grid has the same length.

9. The nanowire sensor of claim 1, wherein the substrate has a structure in which a plurality of silicon layers divided by a silicon-germanium or silicon insulating layer are stacked, and the nanowire grid is formed with a stacked structure.

10. The nanowire sensor of claim 1, further comprising an underwater gate electrode formed over the substrate, wherein the underwater gate electrode directly applies a potential to a solution containing the target material.

11. The nanowire sensor of claim 10, wherein an insulating layer is formed over a region excluding the nanowire region and the underwater gate electrode region.

12. A method for fabricating a nanowire sensor having a nanowire in a network structure, comprising:
   sequentially forming an insulating layer and a silicon layer over a substrate;
   forming a source electrode region, a drain electrode region and a nanowire pattern over the silicon layer using a lithography process;
   implanting ions into the source electrode region and the drain electrode region;
   removing a lower support layer of the nanowire pattern through a wet etching process;
   forming a gate insulating layer outside the source electrode region, the drain electrode region and the nanowire;
   forming a metal electrode over the source electrode region and the drain electrode region;
   forming an upper insulating layer over the metal electrode of the nanowire, and removing the upper insulating layer to expose the gate insulating layer of the nanowire; and
   fixing a detection material, which is to react with a target material injected from outside, to the exposed nanowire pattern,
   wherein the nanowire pattern is formed in a network structure in which patterns of intersections are repeated between the source electrode region and the drain electrode region.

13. The method of claim 12, wherein the forming of the source electrode region, the drain electrode region and the nanowire pattern is performed through any one of electron-beam lithography, nano-implant, ion-beam lithography, X-ray lithography, extreme ultra-violet lithography and photolithography.

14. The method of claim 12, wherein the forming of the metal electrode comprises forming an underwater gate electrode over the lower insulating layer formed over the substrate.

15. The method of claim 14, further comprising forming a channel, through which a fluid containing the target material flows, in the nanowire pattern and the underwater gate electrode, after the fixing of the detection material.

16. The method of claim 12, wherein in the forming of the insulating layer and the silicon layer, the silicon layer is doped with an n-type or p-type material, depending on types and electrochemical characteristics of the target material.

17. The method of claim 12, wherein the removing of the lower support layer of the nanowire pattern comprises forming an oxide layer over the silicon layer and removing the oxide layer.

18. A nanowire sensor having a nanowire in a network structure, comprising:
   source and drain electrodes formed over a substrate;
   a nanowire formed between the source and drain electrodes and having a network structure in which patterns of intersections are repeated; and
   a detection material fixed to the nanowire and selectively reacting with a target material introduced from outside,
   wherein the nanowire has a width of 5 nm to 1 µm, and a selective reaction between the detection material and the target material occurs at the top, both sides, and the bottom of the nanowire.

* * * * *